US010054500B2

(12) United States Patent
Ahmad

(10) Patent No.: US 10,054,500 B2
(45) Date of Patent: Aug. 21, 2018

(54) SYSTEM FOR DETERMINING THERMAL TRANSMITTANCE AND THERMAL RESISTANCE OF BUILDING WALLS ASSEMBLIES UNDER DYNAMIC WEATHER CONDITIONS

(71) Applicant: KING FAHD UNIVERSITY OF PETROLEUM AND MINERALS, Dhahran (SA)

(72) Inventor: Aftab Ahmad, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 382 days.

(21) Appl. No.: 14/864,388

(22) Filed: Sep. 24, 2015

(65) Prior Publication Data

US 2017/0089771 A1    Mar. 30, 2017

(51) Int. Cl.
  *G01K 17/20*    (2006.01)
  *G01N 25/18*    (2006.01)

(52) U.S. Cl.
  CPC ............. *G01K 17/20* (2013.01); *G01N 25/18* (2013.01)

(58) Field of Classification Search
  CPC .......................................... G01K 17/00–17/04
  See application file for complete search history.

(56) References Cited

U.S. PATENT DOCUMENTS

2014/0142884 A1    5/2014    Ahmad et al.

FOREIGN PATENT DOCUMENTS

| CA | 2 870 379 A1 | 10/2013 |
|---|---|---|
| FR | 2 907 215 A1 | 4/2008 |

OTHER PUBLICATIONS

Gracia, et al. ("Dynamic thermal performance of alveolar brick construction system." Energy Conversion and Management, vol. 52, No. 7, 2011, pp. 2495-2500., doi:10.1016/j.enconman.2011.01.022.).*

Baker ("Evaluation of round-Robin testing using the PASLINK test facilities." Building and Environment, vol. 43, No. 2, 2008, pp. 181-188., doi:10.1016/j.buildenv.2006.10.012.).*

Wang, et al. ("A data analysis method for detecting wall thermal resistance considering wind velocity in situ." Energy and Buildings, vol. 42, No. 10, 2010, pp. 1647-1653., doi:10.1016/j.enbuild.2010.04.007).*

Alcamo, et al ("A new test cell for the evaluation of thermo-Physical performance of facades building components." International Journal of Sustainable Energy, vol. 33, No. 4, 2013, pp. 954-962., doi:10.1080/14786451.2013.796943).*

Harrison, S & Collins, Michael. "Queen's University Solar Calorimeter—Design, Calibration, and Operating Procedure", 25th Annual SESCI / NORSUN Conference, 1999.*

(Continued)

*Primary Examiner* — Clayton E Laballe
*Assistant Examiner* — Leon W Rhodes, Jr.
(74) *Attorney, Agent, or Firm* — Oblon, McClelland, Maier & Neustadt, L.L.P.

(57) ABSTRACT

A system to determine thermal properties of wall assemblies under dynamic weather conditions is presented. The system comprises a house-like structure with a suite of measurement devices to measure temperatures, heat fluxes, and weather conditions. The data is recorded over several days, and employed in the calculations for the thermal transmittance and thermal resistance of the wall assembly.

20 Claims, 9 Drawing Sheets

(56) References Cited

OTHER PUBLICATIONS

M.R. Collins, S.J. Harrison "The effects of calorimeter tilt on the inward-flowing fraction of absorbed solar radiation in a Venetian blind", ASHRAE Transactions 107 (2001) 677-683.*
Baker, P., "In situ U-value measurements in traditional buildings—preliminary results", Historic Scotland, Glasgow Caledonian University, URL: http://www.historic-scotland.gov.uk/technicalpaper2.pdf, pp. 1-15, (Oct. 2008).

* cited by examiner

SYSTEM FOR DETERMINING THERMAL TRANSMITTANCE AND THERMAL RESISTANCE OF BUILDING WALLS ASSEMBLIES UNDER DYNAMIC WEATHER CONDITIONS

BACKGROUND OF THE INVENTION

Technical Field

The present invention relates to a system for determining thermal properties of wall assemblies under dynamic weather conditions. The system comprises a house-like structure with a suite of measurement devices to measure temperatures, heat fluxes, and weather conditions.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Energy concerns are critical to the modern society. Therefore, the proper use of thermally efficient wall assemblies can reduce the energy consumption in buildings. To achieve this goal, the thermal transmittance and thermal resistance of wall assemblies must be known. These thermal properties are usually determined with equipment, such as guarded hot plates, and guarded hot boxes, and by methods (PARONEN, M, Canada Patent Application 2870379; AHMAD, A., U.S. patent application Ser. No. 13/681,327—each incorporated herein by reference in its entirety) which test wall assemblies under controlled conditions. Hence, the results are valid only for specific test conditions, and can be a poor predictor of performance if the conditions of use vary from those of the test.

The actual thermal performance of a material depends on system effects, airflow, and its orientation to the sun. For example, the buildings could be constructed in a way that does not replicate the method used during the testing of the material. Airflow through a structure, driven by wind, stack effect, and mechanical equipment, can also transport significant amounts of heat. Heat flow varies over time as the outdoor air temperature varies (on an hourly, daily, and seasonal basis) and as the sun heats the exterior surfaces. These dynamic variations are important for the accurate determination of thermal performance of a material.

In view of the forgoing, the objective of the present invention is to provide a system and a method for determining thermal transmittance and thermal resistance.

BRIEF SUMMARY OF THE INVENTION

According to the first aspect, the present invention relates to a system comprising (i) a structure with a roof, floor and at least four walls, where the roof, the floor and the walls are rigidly connected to one another to enclose an interior space, (ii) at least one interior heat flux sensor, which has a sensing side touching an interior surface of at least one wall to measure heat flux, q, through the wall, (iii) a first temperature recording device to measure interior ambient temperature, $T_I$, (iv) a second temperature recording device to measure exterior ambient temperature, $T_E$, and (v) an interior space control unit which has a computer electrically connected to the first temperature recording device, the second temperature recording device, and the at least one heat flux sensor, and configured to calculate thermal transmittance, U, of the wall.

In one embodiment, the space control unit comprises a cooler, which has built-in thermostat to control the fixed interior temperature, $T_I$.

In another embodiment, the system has at least an anemometer, which is removably attached to the roof, to measure wind speed, V, wind vane to measure direction of the wind and/or a pyranometer to measure solar radiation flux density. The anemometer, wind vane, and pyranometer are electrically connected to the computer.

In one embodiment, the system has a third temperature recording device that has (i) a plurality of interior temperature sensors with their sensing sides touching the interior surface of the wall to measure temperature, $T_C$, (ii) a plurality of exterior temperature sensors with their sensing sides touching the exterior surface of the wall to measure temperature, $T_H$, and (iii) the interior space control unit electrically connected to the third temperature recording device- and configured to calculate thermal resistance, R, of the wall.

In one embodiment, the computer has circuitry to calculate thermal transmittance, U.

In one embodiment, the computer calculates a wind chill factor that is based on measured wind speed and exterior ambient temperature data.

In one embodiment, the computer has circuitry to calculate thermal resistance, R.

In one embodiment, the structure has a length, breadth, and height of 2-10 m.

In one embodiment, the thickness of the walls is 20-60 cm.

In one embodiment, the structure is made of a material comprising at least one material selected from the group consisting of concrete, steel, gypsum, wood, clay, and insulation.

In one embodiment, the structure has at least one wall with an aperture, and the aperture is configured to fit a pre-fitted removable wall piece to seal the interior space from the exterior of the structure. The pre-fitted removable wall piece is removably and releasably attachable to the aperture.

In one embodiment, there is at least one interior heat flux sensor touching the interior surface of the pre-fitted removable wall piece to measure heat flux, q.

In one embodiment, the system further has (i) a third temperature recording device that has a plurality of interior temperature sensors with their sensing sides touching the interior surface of the pre-fitted removable wall piece to measure temperature, $T_C$, (ii) a plurality of exterior temperature sensors with their sensing sides touching the exterior surface of the pre-fitted removable wall piece to measure temperature, $T_H$, and (iii) the interior space control unit electrically connected to the third temperature recording device and configured to calculate thermal resistance, R, of the pre-fitted removable wall piece.

In one or more embodiments, the pre-fitted removable wall piece is made of a material comprising at least one material selected from the group consisting of concrete, steel, gypsum, wood, clay, and insulation.

In one or more embodiments, the pre-fitted removable wall piece has a length, breadth, and height of 0.5-1.5 m.

In one or more embodiments, the thickness of the pre-fitted removable wall piece is 5-60 cm.

In one or more embodiments, the pre-fitted removable wall piece is connected to the structure with at least one connector plate.

According to the second aspect, the present invention relates to a method for determining thermal transmittance of walls by employing the computer to record the data that includes the temperatures from the first, and second temperature recording devices, the heat flux from the at least one heat flux sensor, for up to 100 days, and calculating the thermal transmittance with the recorded data.

According to the third aspect, the present invention relates to a method for determining thermal resistance of walls employing the computer to record the data that includes the temperatures from the third temperature recording device and the heat flux from the at least one heat flux sensor for up to 100 days, and calculating the thermal resistance with the recorded data.

According to the fourth aspect, the present invention relates to a method for comparing the thermal resistance of a first structure with a first pre-fitted removable wall piece and a second structure with a second pre-fitted removable wall piece, comprising (i) measuring the heat flux with at least one heat flux sensor, the temperature of the interior and exterior surface of the pre-fitted removable wall piece with the third temperature recording device, (ii) recording the measured heat flux, the temperature of the interior and exterior wall surface for up to 100 days with the first structure to form a first recorded data set, and with the second structure to form a second recorded data set, (iv) calculating a first thermal resistance from the first recorded data set and a second thermal resistance from the second recorded data set, and (v) comparing the first thermal resistance of the first structure to the second thermal resistance of the second structure.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
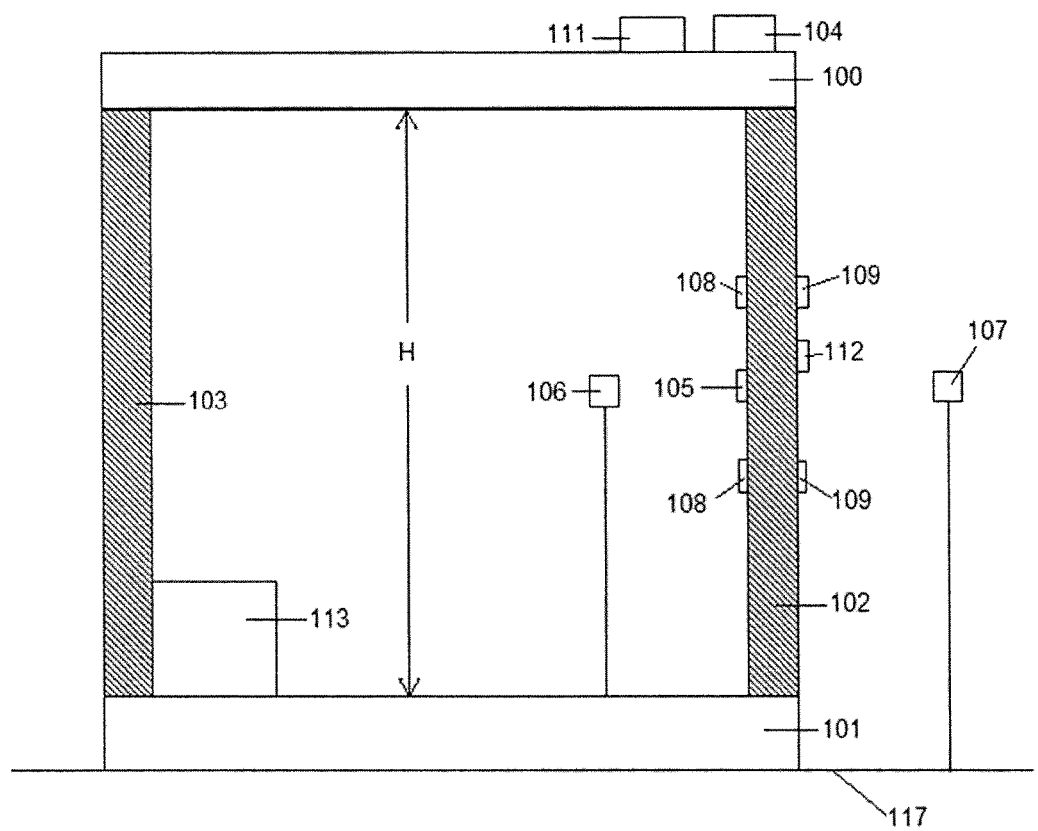
FIG. 1 is a diagrammatic side view of a system for determining thermal transmittance and thermal resistance according to the present invention.

Embodiments of the present disclosure will now be described more fully hereinafter with reference to the accompanying drawings, in which some, but not all embodiments of the disclosure are shown. Referring now to the drawings, wherein like reference numerals designate identical or corresponding parts throughout the several views.

The present invention relates to a system that determines thermal resistance and thermal transmittance of wall assemblies in a structure under dynamic weather conditions. The system has a simple design and can be used to evaluate the actual thermal performance of wall assemblies. This system is easy to operate and inexpensive. One object of the present disclosure is to use the system, in one or more of its embodiments, to generate a database of thermal performance of wall assemblies, allowing architects and engineers to compare and select wall assemblies when designing energy efficient buildings.

Figure 2:
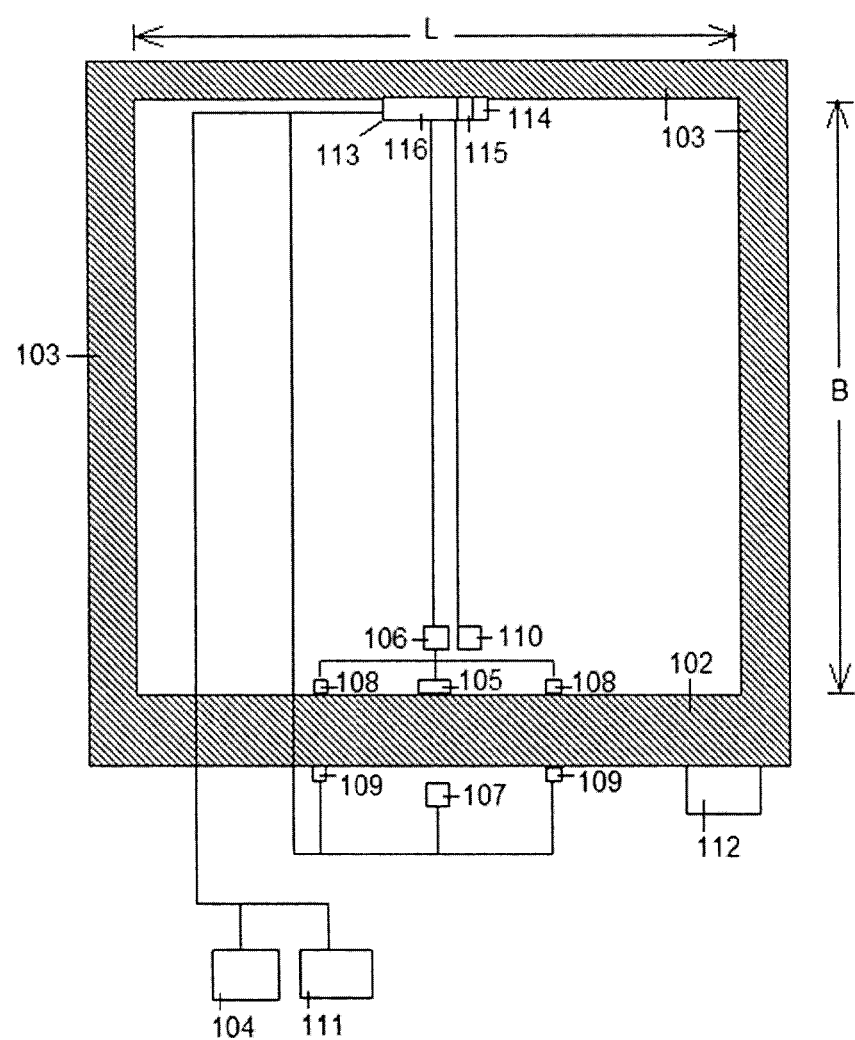
FIG. 2 is a diagrammatic top view of the system.

The system for determining thermal transmittance and thermal resistance of building walls under dynamic weather conditions is shown in FIGS. 1 and 2. The structure includes a roof 100, a floor 101, a wall 102 where its thermal properties are determined, and three other walls 103. It is envisioned that the thermal properties of multiple walls in the structure could be determined in alternative embodiments. The roof, floor, and walls are rigidly connected to enclose an interior space. In one or more embodiments, the structure rests on the ground 117. In one or more embodiments, the structure has a length, L, breadth, B, and height, H, dimensions of 2-10 m, preferably 2-8 m, more preferably 2-4 m, for each dimension. In a preferred embodiment, the structure is a cube. This configuration is representative of a shape of structure which fulfils the requirements of the basic principles of the invention. It is envisioned that alternative shapes of the structure may be used including, but not limited to, a cuboid, a T-shape, a L-shape, a segmented cone, a segmented cylinder, a segmented dome, a rectangular prism, a triangular prism, a square pyramid, a rectangular pyramid, and a triangular pyramid.

In one or more embodiments, the structure is made or fabricated of a material comprising at least one material selected from the group consisting of concrete, iron, wood, gypsum, granite, marble, glass, sand, clay, and insulation. In one or more embodiments, the structure is made from the same material. In one embodiment, the roof, floor, and walls are made from one homogenous layer of material. In a preferred embodiment, the roof, floor, and walls have multiple layers of material. In a preferred embodiment, the multiple layers are adhesively attached to one another. In another embodiment, construction nails pierce through the multiple layers, holding them together. In one embodiment, each layer is made of the same material. In another embodiment, each layer is a different material. In one or more embodiments, bricks are used to build the structure. In one embodiment, the bricks are hollow. In another embodiment, the bricks are solid. In a preferred embodiment, the roof, the floor, and three walls are made of the same material or the same combination of materials, and the fourth wall is made from a material or a combination of materials that differs from the composition of the roof, the floor, and the three walls. In this scenario, the composition of the fourth wall can be interchanged to isolate and test the material used in its construction for ascertaining its thermal properties.

In one or more embodiments, thermal insulation is included in the structure. Forms of thermal insulation include, but are not limited to, blankets, fibrous boards, foam boards, foam blocks, sprayed foams, foamed-in-place materials, foam beads, loose-fill materials, gas bubbles, reflective foils, and reflective films. In a preferred embodiment, foam boards are used. Examples of thermal insulation material include, but are not limited to plastics, cellulose, fiberglass, mineral wool, air, aluminum, vermiculite, and perlite. Examples of plastic insulation material include, but are not limited to, polystyrene, polyethylene, polyisocyanurate, polyurethane, and polyethylene terephthalate. In a preferred embodiment, polystyrene foam boards are used.

Roofs of any design or shape may be used. Examples of roof include, but are not limited to, a flat roof, a gable roof, a gambrel roof, a shed roof, a hipped roof, a pyramid hipped roof, a hemispherical dome roof, and a mansard roof. In general, the roof is shaped according to the shape of the structure. The possible shapes of the roof include, but are not limited to, a circle, an ellipse, an oval, and a polygon. In one or more embodiments, the roof is 20-80 cm thick, preferably 30-70 cm, more preferably 30-60 cm.

In one or more embodiments, each wall is 20-60 cm thick, preferably 20-50 cm, more preferably 20-40 cm. In one embodiment, each wall has the same thickness. In another embodiment, the thicknesses of the walls differ. In one embodiment, at least one wall is 20-40 cm thick, preferably 20-35 cm, more preferably 20-30 cm, and the other walls are 41-60 cm thick, preferably 41-55 cm, more preferably 41-50 cm. In another embodiment, at least one wall is 20-40 cm thick, preferably 25-40 cm, more preferably 30-40 cm, and the other walls are 41-60 cm thick, preferably 45-60 cm, more preferably 50-60 cm.

In general, the floor is shaped according to the shape of the structure. In one or more embodiments, the shape of the floor includes, but is not limited to, a circle, an ellipse, an oval, and a polygon. In one or more embodiments, the floor is 10-80 cm thick, preferably 15-70 cm, more preferably 15-60 cm. In a preferred embodiment, the floor is bare. In one embodiment, the floor is tiled. Examples of tiles include, but are not limited to, ceramic tiles, glass tiles, wood tiles, stone tiles, and concrete tiles. In a preferred embodiment, ceramic tiles are used. The possible shape of each tile includes, but is not limited to, a polygon, a circle, an oval, and an ellipse. In one embodiment, the tile is a square. Each tile is connected to one another and the floor with adhesive, which include, but are not limited to, organic mastics, sanded grout, mortar, latex, acrylic, and epoxy.

The following devices represent a collection of devices which can fulfill the requirements of the basic principles of the invention.

An interior heat flux sensor 105 with a sensing side touching an interior surface of the wall 102 measures heat flux, q. Examples of a heat flux sensor include, but are not limited to, a circular-foil gauge, a thin-film thermopile, and a flat plate sensor. In a preferred embodiment, flat plate sensors are used. In one or more embodiments, the heat flux sensor is attached to at least one of the walls with an adhesive. Examples of adhesives include, but are not limited to, thermal adhesive, thermal grease, and tape. Examples of tape include, but are not limited to, electrical tape, double-sided tape, foil tape, polyester tape, and masking tape. In a preferred embodiment, the heat flux sensor is attached to the wall with thermal grease. In an alternative embodiment, the heat flux sensor is bolted to the wall. In one embodiment, the sensing side of the heat flux sensor has multiple welded metal pins that fit into multiple wall openings such that the sensor protrudes outwardly from the wall. It is envisioned that the heat flux sensors should be located about half-way between the sides of the wall, and the floor and the ceiling, away from the thermal bridge locations such as corners. In one of more embodiments, the sensor is installed 0.5-5 m from the surface of the floor, preferably 0.5-4 m, more preferably 0.5-1.5 m, along the wall vertical axis that is offset by 0-5 m, preferably 0-4 m, more preferably, 0-0.5 m from the center of the wall.

A first temperature recording device 106 measures the interior ambient temperature, $T_I$. In one or more embodiments, the first temperature recording device is placed in a radiation shield. In one or more embodiments, the radiation shield containing the first temperature device is bolted to a first end of a vertical rod, with a second end of the rod bolted to the floor. The second end of the rod is located along a horizontal axis that is offset by 0-5 m, preferably 0-4 m, more preferably, 0-0.5 m from the center of the floor. The rod is 0.5-5 m tall, preferably 0.5-4 m, more preferably 0.5-1.5 m. The highest point of the first temperature recording device is located 10-100 cm from the heat flux sensor, preferably 20-80 cm, more preferably 20-70 cm. In one embodiment, the second end of the vertical rod is bolted to the interior surface of the roof. The second end of the rod is located along a horizontal axis that is offset by 0-5 m, preferably 0-4 m, more preferably, 0-0.5 m from the center of the interior surface of the roof. The rod is 0.5-9.5 m long, preferably 4-9.5 m, more preferably 8.5-9.5 m. The lowest point of the first temperature recording device is located 10-100 cm from the heat flux sensor, preferably 20-80 cm, more preferably 20-70 cm. In an alternative embodiment, the first temperature recording device is placed in the radiation shield mounted to a first end of a horizontal post. A second end of the post is bolted onto the interior wall surface. The post is 1-100 cm long, preferably 5-80 cm, more preferably 5-50 cm, and located 5-100 cm, preferably 5-80 cm, more preferably, 5-50 cm from a corner of the wall. The first temperature recording device is located 0.5-5 m, preferably 0.5-4 m, more preferably 0.5-1.5 m from the floor.

A second temperature recording device 107 measures exterior ambient temperature, $T_E$. In one or more embodiments, the temperature recording device is placed in a radiation shield. In one or more embodiments, the radiation shield containing the second temperature recording device is bolted to a first end of a vertical rod, with a second end of the vertical rod attached to the ground with pegs. The second end of the rod is located along a horizontal axis that is offset by 0-5 m, preferably 0-4 m, more preferably, 0-0.5 m from the center of the floor. The rod is 0.5-5 m tall, preferably 0.5-4 m, more preferably 0.5-1.5 m. The highest point of the second temperature recording device is 1-100 cm from the wall, preferably 5-80 cm, more preferably 5-50 cm. In an alternative embodiment, the second temperature recording device is placed in the radiation shield which is bolted onto the exterior wall surface. The second temperature recording device is located 0.5-5 m, preferably 0.5-4 m, more preferably 0.5-1.5 m from the ground, and 5-100 cm, preferably 5-80 cm, more preferably, 5-50 cm from a corner of the wall, and is 1-100 cm from the wall, preferably 5-80 cm, more preferably 5-50 cm. In an alternative embodiment, the second temperature recording device is placed in the radiation shield mounted to a first end of a horizontal post. A second end of the post is bolted onto the exterior wall surface. The post is 1-100 cm long, preferably 5-80 cm, more preferably 5-50 cm, and located 5-100 cm, preferably 5-80 cm, more preferably, 5-50 cm from a corner of the wall. The second temperature recording device is located 0.5-5 m, preferably 0.5-4 m, more preferably 0.5-1.5 m from the floor. In one embodiment, the second temperature recording device is a plurality of temperature recording devices to measure the exterior ambient temperatures, which are then averaged to account for sunlight heating each face of the structure unevenly. In one embodiment, the temperature recording devices may be located outside each wall, for example a second temperature recording device located outside of each of the four walls of the structure.

A third temperature recording device with a plurality of interior temperature sensors 108 releasably attached to the wall surface measure $T_C$, and a plurality of exterior temperature sensors 109 releasably attached to the wall surface to measure $T_H$. The interior temperature sensors are located within a radius of 5-50 cm from the heat flux sensor, preferably 10-40 cm, more preferably 10-30 cm. The exterior temperature sensors are located on a circumference of a circle with a radius of 5-50 cm, preferably 10-40 cm, more preferably 10-30 cm, and the centrally disposed horizontal axis of the circle passes through the center of the heat flux sensor. The interior temperature sensors are evenly spaced on the circumference of the circle such that the shortest distance measured between these temperature sensors are the same. The exterior temperature sensors adopt the same arrangement. In a preferred embodiment, there are four interior temperature sensors and four exterior temperature sensors.

The types of temperature recording devices and sensors include, but are not limited to, thermocouples, resistance temperature detector, and thermistors. In a preferred embodiment, thermocouples are used. The type of thermocouples used in the first, second, and third temperature recording devices include, but are not limited to B, C, D, E, G, J, K, M, N, R, S, and T. The designs of thermocouples include gasket thermocouples, bayonet thermocouples, and weld pad thermocouples. In a preferred embodiment, the first and second temperature recording devices are bayonet thermocouples.

For the third temperature recording device, the entire measurement area of the temperature sensors must be in contact with the surface in order to assure an accurate measurement. In one embodiment, self-adhesive pads are used to attach the temperature sensors to the wall surface. In a preferred embodiment, the gasket thermocouples are attached to a stud welded to the surface of the wall. In another embodiment, the bayonet thermocouples are inserted through a drilled opening to a depth of 1-10 cm, preferably 1-5 cm, more preferably 1-3 cm from the wall surface.

A hygrometer 110 measures humidity, which may cause condensation forming on walls and ceilings that are colder than the ambient temperature and potentially damaging wall assemblies. Examples of hygrometers include, but are not limited to, capacitive humidity sensors, resistive humidity sensors, thermal conductivity humidity sensors, gravimetric hygrometer. In a preferred embodiment, thermal conductivity humidity sensor is used. In one or more embodiments, there is at least one hygrometer located in the interior of the structure, the exterior of the structure or both. In a preferred embodiment, there is one hygrometer in the interior. The hygrometer could be removably attached to the walls, for example, with bolts, and/or adhesives such as glue and/or tape. In a preferred embodiment, the hygrometer is removably attached on the first end of the stand, and the second end of the stand is bolted to the floor. The hygrometer is located in a radius of 5-100 cm, preferably 5-80 cm, more preferably 5-60 cm from the first temperature recording device.

In a preferred embodiment, an anemometer 104 is disposed on the roof to measure wind speed, V. Examples of anemometers include, but are not limited to, cup anemometers, vane anemometers, and sonic anemometers. In a preferred embodiment, a cup anemometer is used. In one embodiment, the anemometer is bolted to a first end of a mounting pole, and a second end of the pole is bolted to the roof. The height of the mounting pole is 1.5-2.5 m, preferably, 1.6-2.3 m, more preferably 1.7-2.0 m. In one embodiment, the anemometer is bolted directly to the roof In some seasons, wind speed can affect the ambient temperatures. Therefore, measuring wind speed is useful for calculating wind chill, which may impact the thermal properties of buildings. Therefore, it is advantageous for the system to measure and take wind speed into account during testing periods.

In a preferred embodiment, a wind vane 111 is mounted on the roof to measure wind direction. The wind vane is bolted to a first end of a mounting pole, and a second end of the pole is bolted to the roof. The height of the mounting pole is 1.5-2.5 m, preferably, 1.6-2.3 m, more preferably 1.7-2.0 m.

A pyranometer 112 measures solar radiation flux density. Prolonged exposure to sunlight may affect the integrity of the structure, so the solar radiation flux density should be recorded in order to appreciate the thermal properties of the wall obtained during different times of the year. Examples of pyranometers include, but are not limited to semiconductor pyranometers and thermopile pyranometers. In a preferred embodiment, a thermopile pyranometer is used. In a preferred embodiment, the pyrometer is bolted to the wall 102. The pyranometer is located 5-100 cm, preferably 5-80 cm, more preferably, 5-50 cm from the roof, and 5-100 cm, preferably 5-80 cm, more preferably, 5-50 cm from the side of the wall.

The amount of precipitation may affect the integrity of the structure and hence the thermal properties. Therefore, it is envisioned that this invention would include instruments, such as rain gauge and snow gauge, to measure the amount of precipitation. The choice of instrument depends on the season. In one embodiment, a rain gauge is used to measure liquid precipitation over the four seasons. The rain gauge may be mounted on a first side of a vertical post. In one embodiment, top of the rain gauge extends 5-20 cm, preferably 5-15 cm, more preferably 5-12 cm above the top of the mounting post. The mounting post has a rounded, pointed, or slanted top to avoid upward splash towards the rain gauge. The top of the rain gauge is 0.5-1.6 m, preferably 0.5-1.5 m, more preferably 0.5-1.2 m above the ground. The rain gauge is located 4-20 m, preferably 4-16 m, more preferably 4-8 m from the structure. In another embodiment, a snow gauge is used to measure solid precipitation during winter. The snow gauge is installed in the same manner as the rain gauge. The amount of precipitation is entered manually into a computer 116 in an interior space control unit 113.

The interior space control unit 113 has a cooler 114, a heater 115, which may be electrically connected to the computer 116. The cooler and heater have built-in thermostats to control the interior air temperature, $T_I$. Examples of cooler include, but are not limited to, an air-conditioner and an evaporative cooler. In a preferred embodiment, the air-conditioner is used. Examples of heater include, but are not limited to, a fan-forced heater, a ceramic heater, an infrared heater, and a radiant oil heater. In a preferred embodiment, ceramic heater is used. The control unit, cooler, and heater rest on the floor and are located at the wall opposite wall 102.

Figure 3:
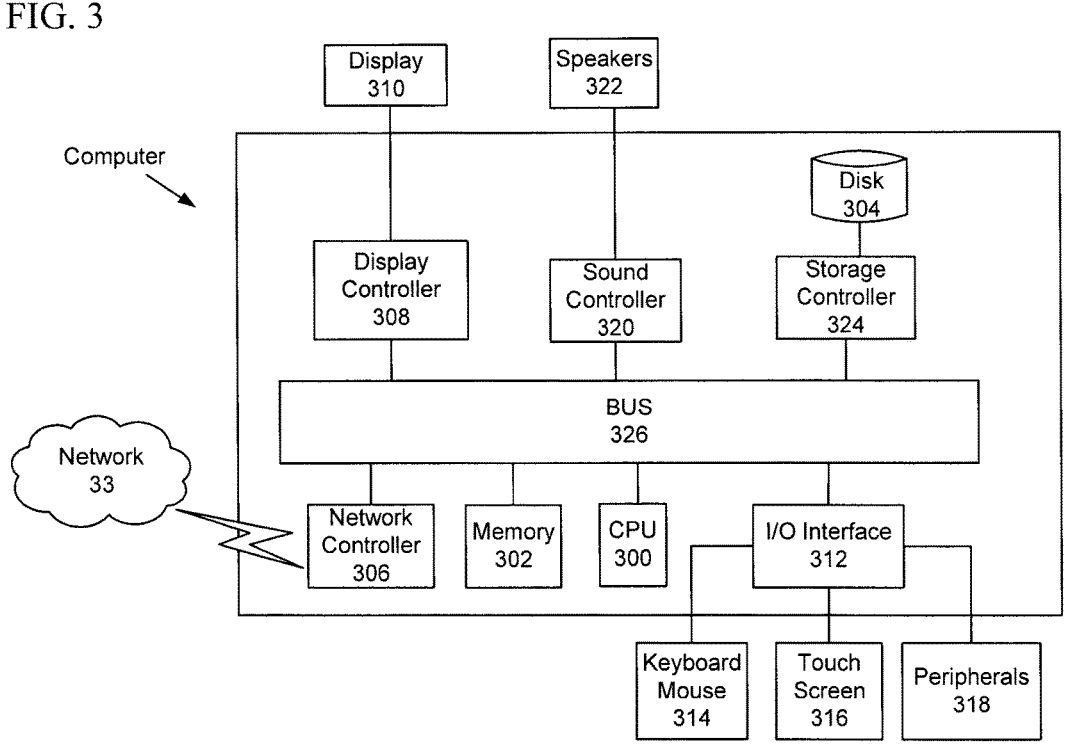
FIG. 3 is a block diagram illustrating components of a computer used in a system for determining thermal transmittance and thermal transmittance according to the present invention.

Next, a hardware description of the computer according to exemplary embodiments is described with reference to FIG. 3. In FIG. 3, the computer includes a CPU 300 which performs the processes described below. The process data and instructions may be stored in memory 302. These processes and instructions may also be stored on a storage medium disk 304 such as a hard drive (HDD) or portable storage medium or may be stored remotely.

Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computer communicates.

Further, the claimed advancements may be provided as a utility application, background daemon, or component of an operating system, or combination thereof, executing in conjunction with CPU 300 and an operating system such as Microsoft Windows 7, UNIX, Solaris, LINUX, Apple MAC-OS and other systems known to those skilled in the art.

The hardware elements in order to achieve the computer may be realized by various circuitry elements, known to those skilled in the art. For example, CPU 300 may be a Xenon or Core processor from Intel of America or an Opteron processor from AMD of America, or may be other processor types that would be recognized by one of ordinary skill in the art. Alternatively, the CPU 300 may be implemented on an FPGA, ASIC, PLD or using discrete logic circuits, as one of ordinary skill in the art would recognize. Further, CPU 300 may be implemented as multiple processors cooperatively working in parallel to perform the instructions of the inventive processes described above.

The computer in FIG. 3 also includes a network controller 306, such as an Intel Ethernet PRO network interface card from Intel Corporation of America, for interfacing with network 33. As can be appreciated, the network 33 can be a public network, such as the Internet, or a private network such as an LAN or WAN network, or any combination thereof and can also include PSTN or ISDN sub-networks. The network 33 can also be wired, such as an Ethernet network, or can be wireless such as a cellular network including EDGE, 3G and 4G wireless cellular systems. The wireless network can also be WiFi, Bluetooth, or any other wireless form of communication that is known.

The computer further includes a display controller 308, such as a NVIDIA GeForce GTX or Quadro graphics adaptor from NVIDIA Corporation of America for interfacing with display 310, such as a Hewlett Packard HPL2445w LCD monitor. A general purpose I/O interface 312 interfaces with a keyboard and/or mouse 314 as well as a touch screen panel 316 on or separate from display 310. General purpose I/O interface also connects to a variety of peripherals 318 including printers and scanners, such as an OfficeJet or DeskJet from Hewlett Packard.

A sound controller 320 is also provided in the computer, such as Sound Blaster X-Fi Titanium from Creative, to interface with speakers/microphone 322 thereby providing sounds and/or music.

The general purpose storage controller 324 connects the storage medium disk 304 with communication bus 326, which may be an ISA, EISA, VESA, PCI, or similar, for interconnecting all of the components of the computer. A description of the general features and functionality of the display 310, keyboard and/or mouse 314, as well as the display controller 308, storage controller 324, network controller 306, sound controller 320, and general purpose I/O interface 312 is omitted herein for brevity as these features are known.

The computer has software stored in the memory and executable by the CPU. In one embodiment, the computer is electrically connected to at least one of the first, second, and third temperature recording devices, the at least one heat flux sensor, the hygrometer, the wind vane, the pyranometer, the anemometer, the cooler, and the heater. In one embodiment, electrical wires connect the devices to the computer. In a preferred embodiment, the devices communicate wirelessly to the computer and vice versa.

Under dynamic weather conditions, heat flow to and within the structure vary over time as the outdoor air temperature varies (on an hourly, daily, and seasonal basis) and as the sun heats the exterior surfaces. Therefore, it is intended that in one or more embodiments, the structure is designed to take these dynamic factors into account when determining the thermal performance of a material.

Figure 8:
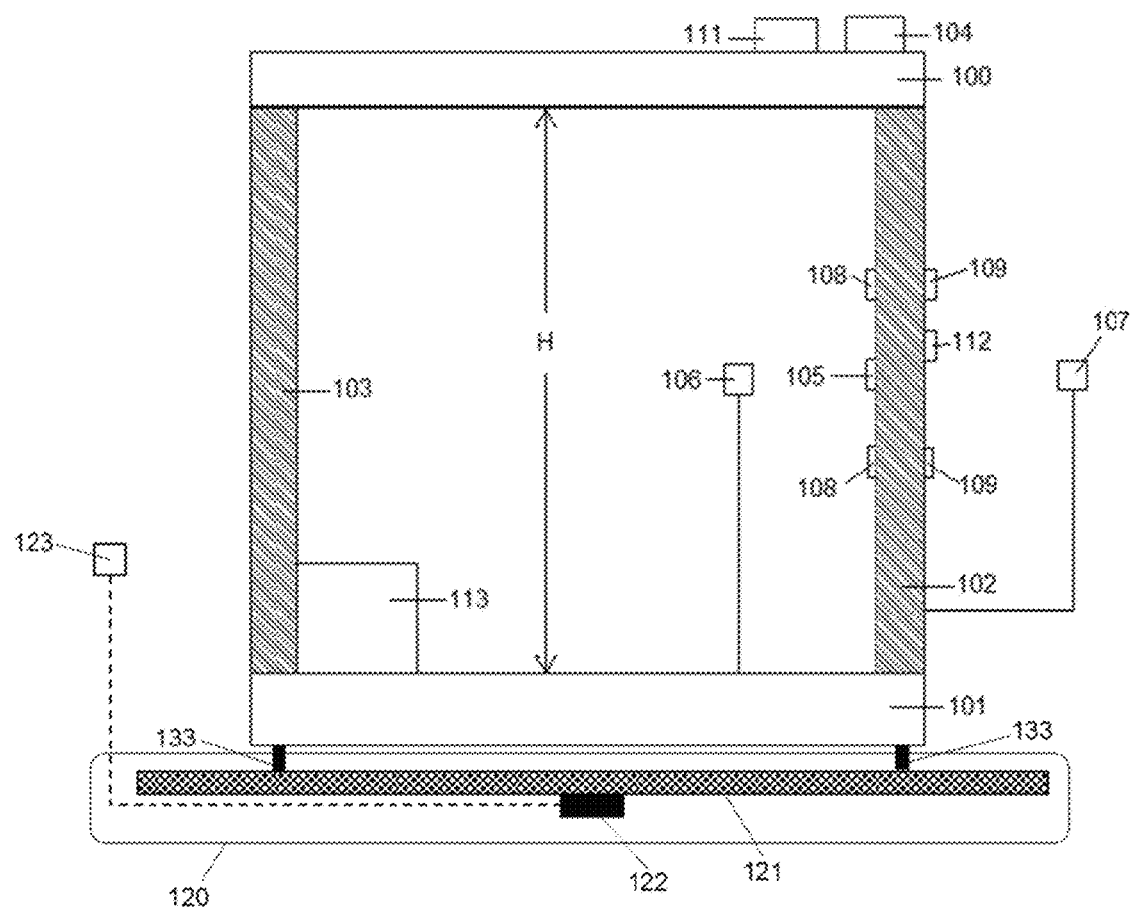
FIG. 8 is a diagrammatic side view of a system for determining thermal transmittance and thermal resistance according to the present invention, wherein the system includes a rotating device.

As shown in FIG. 8, in one or more embodiments, the structure may be installed on a rotating device 120 so that the structure can rotate 360° about its vertical axis. The components of a rotating device include, but are not limited to, a rotating device control panel 123, a motor 122, at least one brake, and a rotating platform 121. The components are electrically connected to one another. In one or more embodiments, the rotating device 120 rests on the ground. In a preferred embodiment, the structure is arranged on the rotating device in a way that a centrally disposed vertical axis through the device passes through the center of the floor first and then the roof. In a preferred embodiment, the floor of the structure is bolted to the rotating platform. In a preferred embodiment, the size of the rotating platform is larger than the structure, and can take on any shape, including, but are not limited to, a circle, an oval, an ellipse, and a polygon. In a preferred embodiment, the rotating platform is a circle made of steel. In one embodiment, the rotating platform is attached to a bearing set which is mechanically attached to a motor. The bearing set has a first plate which is bolted to the rotating platform. A second plate is bolted the ground. It is envisioned that the plate can take on any shape, including, but is not limited to, a circle, an oval, an ellipse, and a polygon. In a preferred embodiment, the plates are squares. The dimensions of the plates are 0.5-11 m, preferably 0.5-9 m, more preferably 0.5-5 m. In a preferred embodiment, the plates are made of steel. The plates sandwich a raceway containing rolling elements to reduce rotational friction. The elements can take on any of the following shapes: cylindrical, spherical, barrel, needle, spindle, or tapered. The material of the rolling elements includes, but is not limited to, steel, plastic, and ceramic. In a preferred embodiment, stainless steel spherical rolling elements are used.

The rotating device is electrically connected to the computer. In one embodiment, the computer has software stored in the memory and executable by the CPU to record and adjust the speed of rotation. In an alternative embodiment, the speed of rotation is adjusted manually from the control panel.

In one or more embodiments, a solar tracker system is installed on the structure, enabling it to track the sun. The components of the solar tracker system includes, but are not limited to, the pyranometer, a sun tracking algorithm stored in the computer readable memory, and the computer to execute the sun tracking algorithm and coordinate the movement of the rotating device. The computer uses the real-time light intensity readings from the pyranometer to adjust the position of the structure relative to the sun. This arrangement facilitates the study of thermal properties of materials in various orientations relative to the sun, and this information would be useful to architects, contractors, consultants and engineers when they design buildings. In a preferred embodiment, the wall 102 is oriented away from the sun for the duration of measurement. In another embodiment, the wall faces the sun.

Figure 9:
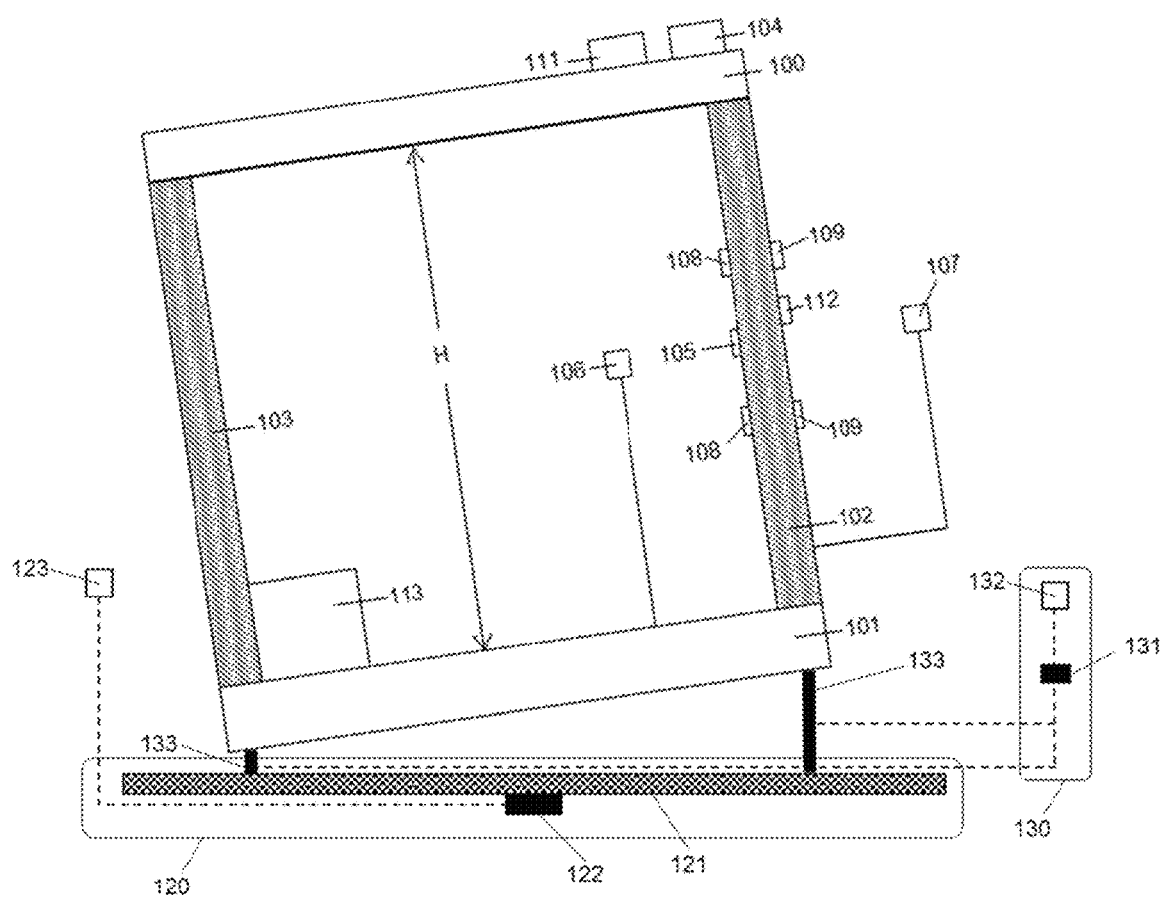
FIG. 9 is a diagrammatic side view of a system for determining thermal transmittance and thermal resistance according to the present invention, wherein the system includes a rotating device and a tilt assembly.

As shown in FIG. 9, in one or more embodiments, the structure is supported on a tilt assembly 130 which is electrically connected to a tilt assembly control panel 132 and mounted on the rotating device 120. The components of the tilt assembly 130 include, but are not limited to, a pump 131, at least one actuator 133, at least one brake, and a tilt assembly control panel 132. The components are electrically connected to one another. In one embodiment, a pneumatic tilt assembly is used. In a preferred embodiment, a hydraulic tilt assembly is used. In one or more embodiments, where the floor has at least four corners, a vertical actuator is connected to each corner. The first end of the vertical actuator is bolted to the floor, and a second end of the vertical actuator is bolted to the rotating platform. The vertical actuators are fluidly connected to a hydraulic pump. Each of the actuator is independently extendable to increase and decrease a length, tilting the structure to either minimize or maximize sunlight intensity. A tilt angle is 45-90°, preferably 55-90°, more preferably 75-90° relative to the horizon.

The tilt assembly is electrically connected to the computer. In one embodiment, the computer has software stored in the memory and executable by the CPU to record and adjust the tilt angle. In an alternative embodiment, the tilt angle is adjusted manually from the control panel.

Figure 4:
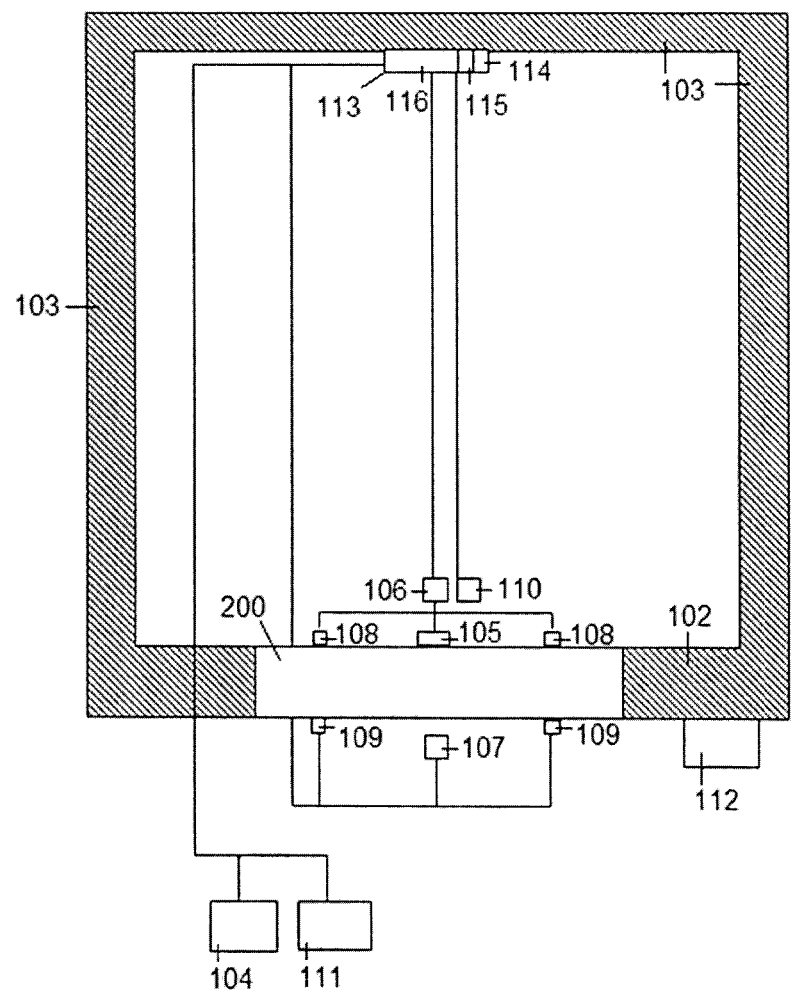
FIG. 4 is a diagrammatic top view of a system with a pre-fitted removable wall piece in one of the walls, where the thermal transmittance and thermal resistance of the pre-fitted removable wall is to be determined by the system.
Figure 5:
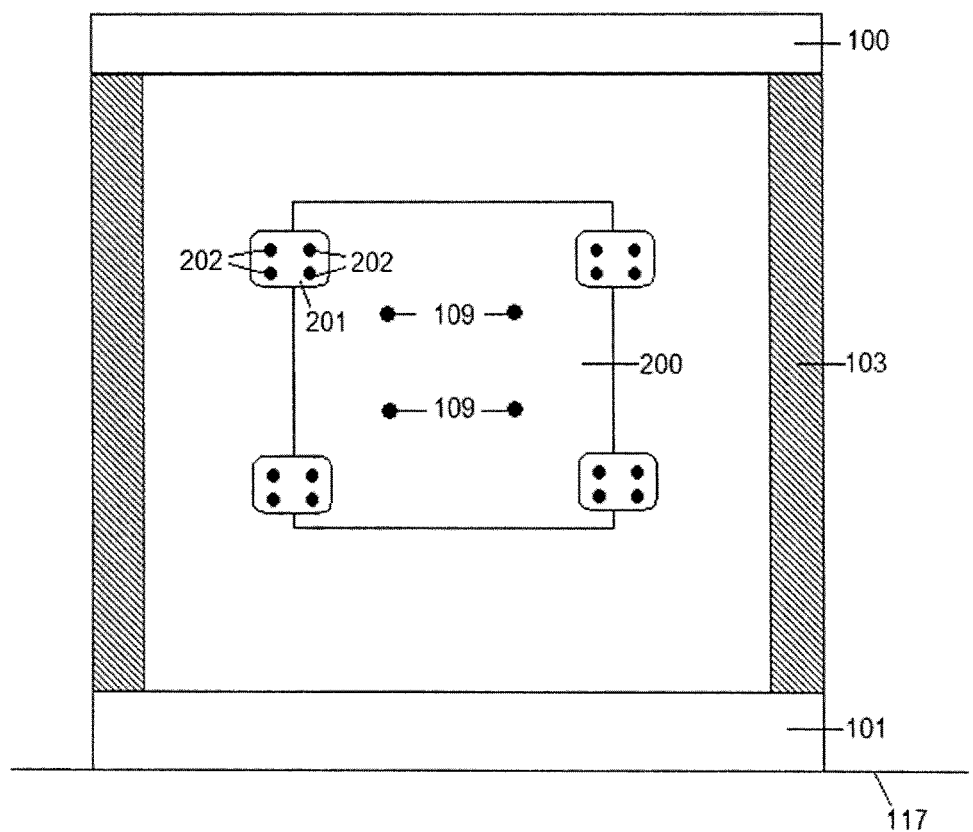
FIG. 5 is a diagrammatic side view of the system with the pre-fitted removable wall piece connected to the wall with connector plates.
Figure 6:
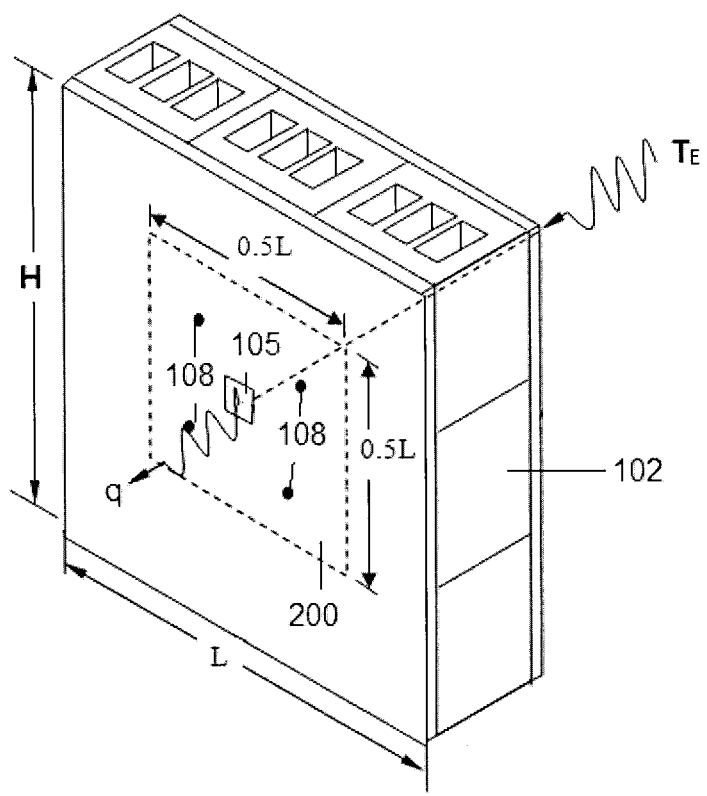
FIG. 6 is a perspective view of the pre-fitted removable wall piece connected to the wall.

This disclosure further relates to a system with an aperture in at least one of the walls (FIGS. 4, 5, and 6). It is envisioned that the aperture can take on any shape, including, but is not limited to, a circle, an oval, an ellipse, and a polygon. In a preferred embodiment, the aperture is shaped like a square. The aperture is configured to fit a pre-fitted removable wall piece 200 to seal the interior space from the exterior of the structure. The pre-fitted removable wall piece has a length, breadth, and height of 0.5-1.5 m, preferably 0.8-1.5 m, more preferably 1-1.5 m. The surface area of the pre-fitted removable wall piece relative to the total surface area of the wall is 0.1-20%, preferably 0.5-15%, more preferably 1-10%, more preferably 1.5-9%, more preferably 2-8%, more preferably 3-7%. In one embodiment, the pre-fitted removable wall piece is made of the same materials as the walls. In another embodiment, the pre-fitted removable wall piece is made of materials which are different from the walls. In one or more embodiments, the pre-fitted removable wall piece material comprises at least one material selected from the group consisting of concrete, steel, gypsum, granite, marble, glass, sand, clay, and insulation.

In one or more embodiments, the pre-fitted removable wall piece is made from one material. In one embodiment, the pre-fitted removable wall piece is made from one homogenous layer of material. In a preferred embodiment, the pre-fitted removable wall piece has multiple layers of material. In one embodiment, the multiple layers are adhesively attached to one another. In another embodiment, construction nails pierce through the multiple layers, holding them together. In one embodiment, each layer is made of the same material. In another embodiment, each layer is a different material. In one or more embodiments, bricks are used to build the pre-fitted removable wall piece. In one embodiment, the bricks are hollow. In another embodiment, the bricks are solid. In one embodiment, the pre-fitted removable wall piece has at two layers of materials with an empty space located in between the two materials. In one embodiment, the two layers may be different such that the layer facing the exterior is different from the layer facing the interior.

In one or more embodiments, the pre-fitted removable wall piece is releasably attached to the aperture. In one or more embodiments, the pre-fitted removable wall piece is connected to the structure using connector plates 201 and screws 202 (FIG. 5). The first half of the plate connector is bolted to the pre-fitted removable wall piece, and the second half of the plate connector is bolted to the wall. In a preferred embodiment, metal plate connectors are used. In one embodiment, there is a connector plate on each corner of the first surface of the pre-fitted removable wall piece. In another embodiment, there is a connector plate on each corner of the first and second surfaces of the pre-fitted removable wall piece. In one embodiment, the pre-fitted removable wall piece is connected to the structure using hinges and screws.

Any gaps between the pre-fitted removable wall piece and the wall may either be covered with a thermal insulation tape and/or filled with the thermal insulation materials mentioned previously. In an alternative embodiment, a pre-fitted removable frame could be installed to cover the gaps. The methods to attach the frame to the wall of the structure include, but are not limited to, nails and/or adhesive paste. The frame material comprises at least one material selected from the group consisting of iron, aluminum, and wood.

In an alternative embodiment, the pre-fitted removable wall piece is permanently attached to the aperture. Examples of material used to seal the wall include, but are not limited to, mortar and adhesive paste are used to seal the gap between the pre-fitted removable wall piece and the wall of the structure.

Figure 7:
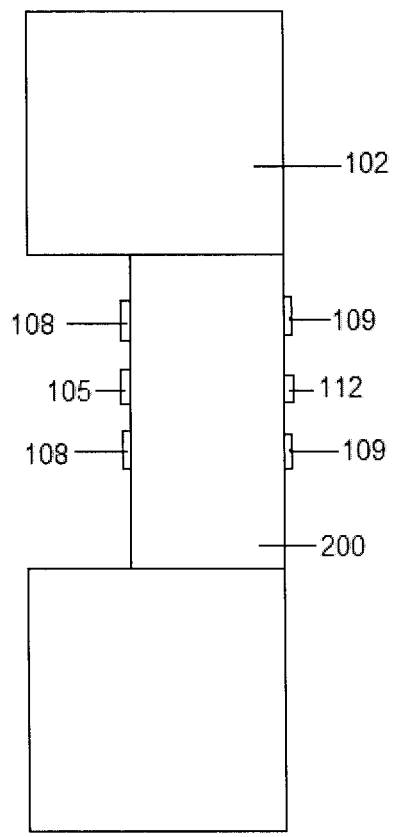
FIG. 7 is a diagrammatic cross-section view of a thin pre-fitted removable wall piece connected to a thicker wall.

This system can accommodate pre-fitted removable wall pieces with various thicknesses. In one or more embodiments, the pre-fitted removable wall piece is 5-60 cm thick, preferably 5-50 cm, more preferably 5-40 cm. In one or more embodiments, the pre-fitted removable wall piece is thinner than the wall and is arranged as shown in FIG. 7.

This disclosure further relates to a method to record data that includes the temperatures from the first, second, and third temperature recording devices, the heat flux from the at least one heat flux sensor, the wind speed from the anemometer, and calculating the thermal properties of the material from the recorded data. In one embodiment, the computer is configured to record the data from the above-mentioned devices when a thermal steady state is reached (the heat flux and surface temperatures are constant over 0.5-3 h, preferably 0.5-2 h, more preferably 0.5-1 h). The data is collected at intervals of 1-120 s, preferably 5-90 s, more preferably 10-60 s. In one embodiment, the data is averaged over 5-30 min, preferably 5-20 min, more preferably 5-10 min. In another embodiment, the data is used as recorded, without further processing. The data is recorded for up to 100 days, preferably 4-90 days, preferably 4-70 days, preferably 4-40 days, more preferably 4-6 days. In order to control the interior air temperature, $T_I$, the cooling and heating outputs of the cooler and heater are adjusted by the respective built-in thermostats. The desired $T_I$ is 15-28° C., preferably 16-25° C., more preferably 18-25° C. The software has the function to calculate thermal transmittance, U, of the wall according to equation (1):

$$U = \frac{\sum_{k=1}^{n} q_k}{\sum_{k=1}^{n} (\Delta T_{ak})} \quad (1)$$

where $\Delta T_a = T_E - T_I$, k and n are integers, with n larger than 1, and $q_1$, $T_{a1}$ refer to the data acquired at the first time point, $q_2$, $T_{a2}$ refer to the data acquired at the second time point, and $q_n$, $T_{an}$ refer to the data acquired at the nth time point.

The software also has the function to calculate thermal resistance, R, of the wall according to equation (2):

$$R = \frac{\sum_{k=1}^{n} (\Delta T_{sk})}{\sum_{k=1}^{n} q_k} \quad (2)$$

where $\Delta T_s = T_H - T_C$, k and n are integers, with n larger than 1, and $q_1$, $T_{a1}$ refer to the data acquired at the first time point, $q_2$, $T_{a2}$ refer to the data acquired at the second time point, and $q_n$, $T_{an}$ refer to the data acquired at the nth time point.

It is envisioned that wind chill may affect the thermal properties of the structure materials. Therefore, in one or more embodiments, the computer calculates the wind chill factor. In one embodiment, the wind chill factor, $T_{WC}$, is $T_{WC} = 13.12 + 0.6215 T_E - 11.37 V^{0.16} + 0.3965 T_E V^{0.16}$.

The disclosure also relates to a method for comparing the thermal resistance of a first structure with a first pre-fitted removable wall piece and a second structure with a second pre-fitted removable wall piece. The method comprises, (i) measuring the heat flux with at least one heat flux sensor, the temperature of the interior and exterior wall surface with the third temperature recording device, for both the first and second structure, (ii) recording the measured heat flux, the temperature of the interior and exterior wall surface, for the first and second system for up to 100 days with the first structure to form a first recorded data set, and with the second structure to form a second recorded data set, (iv) calculating a first thermal resistance from the first recorded data set and a second thermal resistance from the second recorded data set, and (v) comparing the first thermal resistance of the first structure to the second thermal resistance of the second structure. It is envisioned that the method for comparing two pre-fitted removable wall pieces can be extended to a plurality of pre-fitted removable wall pieces. The thermal resistance of each pre-fitted removable wall piece is entered into a database that architects, engineers, and the like could refer to when designing energy efficient buildings. In addition, it is envisioned that the pre-fitted removable wall pieces can differ in the aforementioned shapes, aforementioned thicknesses, and aforementioned materials. In a preferred embodiment, the pre-fitted removable wall pieces have the same shape and thickness, but have different materials.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A system comprising:
   a structure with a roof, a floor and at least four walls, wherein the roof, the floor and the at least four walls are rigidly connected to one another to enclose an interior space;
   at least one interior heat flux sensor, wherein a sensing side of the at least one interior heat flux sensor is in communication with an interior surface of at least one wall to measure a heat flux, q, through the at least one wall;
   a first temperature recording device to measure an interior ambient temperature, $T_I$;
   a second temperature recording device to measure an exterior ambient temperature, $T_E$;
   a rotating device comprising a rotating platform, a motor, and a rotating device control panel, wherein the floor is releasably attached to a surface of the rotating platform;
   a tilt assembly comprising a pump, a tilt assembly control panel, and at least one actuator each with a first end and a second end, wherein the first end of the at least one actuator is releasably attached to the structure and the second end of the at least one actuator is releasably attached to the surface of the rotating platform; and
   an interior space control unit comprising a computer that communicates with the first temperature recording device, the second temperature recording device, the at least one interior heat flux sensor, the rotating device control panel, and the tilt assembly control panel,
   wherein the computer is configured to rotate and/or tilt the structure to a predetermined orientation relative to a position of the sun, and to calculate thermal transmittance, U, of the at least one wall at the predetermined orientation relative to the position of the sun, and
   wherein the predetermined orientation relative to the position of the sun is defined by a tilting angle relative to the horizon and a rotating angle around a vertical axis of the rotating platform.

2. The system of claim 1, wherein the interior space control unit comprises a cooler, wherein the cooler has built-in thermostats to control the interior ambient temperature, $T_I$.

3. The system of claim 1, further comprising:
   an anemometer that is removably attached to the roof to measure a wind speed, V, wherein the anemometer is in communication with the computer.

4. The system of claim 3, wherein the computer comprises circuitry to calculate a wind chill factor based on the wind speed and the exterior ambient temperature.

5. The system of claim 1, further comprising:
a third temperature recording device comprising:
- a plurality of interior temperature sensors, wherein a sensing side of each interior temperature sensor is in communication with the interior surface of each of the at least four walls to measure an interior wall temperature, $T_C$; and
- a plurality of exterior temperature sensors, wherein a sensing side of each exterior temperature sensor is in communication with an exterior surface of each of the at least four walls to measure an exterior wall temperature, $T_H$;
- wherein the computer is in communication with the third temperature recording device to calculate thermal resistance, R, of the at least one wall at the predetermined orientation relative to the position of the sun.

6. The system of claim 4, wherein the computer comprises circuitry to calculate thermal resistance, R, of the at least one wall at the predetermined orientation relative to the position of the sun.

7. The system of claim 1, wherein the computer comprises circuitry to calculate thermal transmittance, U, of the at least one wall at the predetermined orientation relative to the position of the sun.

8. The system of claim 1, wherein each of a length, breadth, and height of the structure is within a range of 2-10 m.

9. The system of claim 1, wherein the structure is made of a material comprising at least one material selected from the group consisting of concrete, steel, gypsum, wood, clay, and an insulation material.

10. The system of claim 1, wherein at least one wall has an aperture configured to fit a pre-fitted removable wall piece to seal the interior space from an exterior of the structure, and the pre-fitted removable wall piece is removably and releasably attached to the aperture.

11. The system of claim 10, wherein the at least one interior heat flux sensor is present in the pre-fitted removable wall piece and the sensing side of the at least one interior heat flux sensor is in communication with an interior surface of the pre-fitted removable wall piece to measure the heat flux, q, through the pre-fitted removable wall piece.

12. The system of claim 10, further comprising:
a third temperature recording device comprising:
- a plurality of interior temperature sensors, wherein a sensing side of each interior temperature sensor is in communication with an interior surface of the pre-fitted removable wall piece to measure an interior wall temperature, $T_C$; and
- a plurality of exterior temperature sensors, wherein a sensing side of each exterior temperature sensor is in communication with an exterior surface of the pre-fitted removable wall piece to measure an exterior wall temperature, $T_H$;
- wherein the interior space control unit is electrically connected to the third temperature recording device and configured to calculate thermal resistance, R, of the pre-fitted removable wall piece.

13. The system of claim 10, wherein the pre-fitted removable wall piece is made of a material comprising at least one material selected from the group consisting of concrete, steel, gypsum, wood, clay, and an insulation material.

14. The system of claim 10, wherein the pre-fitted removable wall piece is connected to the structure with at least one connector plate.

15. The system of claim 1,
wherein the rotating angle is in the range of 0° to 360° around a vertical axis of the rotating platform, and
wherein the tilting angle is in the range of 45° to 90° relative to the horizon.

16. The system of claim 1, further comprising:
a pyranometer that is secured on an exterior of the structure to measure a solar radiation flux density,
wherein the pyranometer is in communication with the computer.

17. The system of claim 1, further comprising:
a wind vane that is removably attached to the roof to measure a wind direction,
wherein the wind vane is in communication with the computer.

18. The system of claim 1,
wherein the structure has a rectangular shape with four corners, and
wherein the tilt assembly comprises four vertical actuators each with a first end and a second end, wherein the first end of each vertical actuator is releasably attached to one corner of the structure and the second end of each vertical actuator is releasably attached to the rotating platform.

19. A method for determining thermal transmittance of at least one wall with the system of claim 1, comprising:
measuring the heat flux with the at least one interior heat flux sensor, the interior ambient temperature with the first temperature recording device, and the exterior ambient temperature with the second temperature recording device;
recording the heat flux, the interior ambient temperature, and the exterior ambient temperature for up to 100 days to form recorded data; and
calculating the thermal transmittance of the at least one wall from the recorded data.

20. A method for determining thermal resistance of at least one wall with the system of claim 5, comprising:
measuring the heat flux with the at least one interior heat flux sensor, the interior wall temperature with the plurality of interior temperature sensors, and the exterior wall temperature with the plurality of exterior temperature sensors;
recording the heat flux, the interior wall temperature, and the exterior wall temperature for up to 100 days to form recorded data; and
calculating the thermal resistance of the at least one wall from the recorded data.

* * * * *